United States Patent [19]

Millequant et al.

[11] Patent Number: 5,447,654
[45] Date of Patent: Sep. 5, 1995

[54] BLEACHING COMPOSITION IN GRANULATED FORM WHICH MAY BE USED FOR BLEACHING HAIR AND PROCESS FOR THE PREPARATION OF THE SAID COMPOSITION

[75] Inventors: Jean-Marie Millequant, Saint-Maur; Caroline Tricaud, Cormeilles en Parisis; Anne Gaboriaud, Le Raincy, all of France

[73] Assignee: L'Oreal, Paris, France

[21] Appl. No.: 217,665

[22] Filed: Mar. 25, 1994

[30] Foreign Application Priority Data

Apr. 5, 1993 [FR] France ................... 93 03995

[51] Int. Cl.$^6$ .............. C01B 15/00; C01B 15/04; C01B 15/055
[52] U.S. Cl. .............. 252/186.25; 252/186.26; 252/186.27; 252/186.3; 252/186.31; 252/186.33
[58] Field of Search .............. 252/186.25, 186.26, 252/186.30, 186.31, 186.32, 186.33, 186.27, 186.28

[56] References Cited

U.S. PATENT DOCUMENTS

| | | | |
|---|---|---|---|
| 3,227,790 | 1/1966 | Bretschneider | 264/117 |
| 4,486,327 | 12/1984 | Murphy et al. | 252/94 |
| 4,915,863 | 4/1990 | Aoyagi et al. | 252/102 |
| 5,002,691 | 3/1991 | Bolkan et al. | 252/186.25 |
| 5,094,827 | 3/1992 | Bertsch-Frank et al. | 423/279 |
| 5,269,962 | 12/1993 | Brodbeck et al. | 252/186.25 |

FOREIGN PATENT DOCUMENTS

| | | |
|---|---|---|
| 2023922 | 11/1970 | Germany . |
| 3434468 | 3/1986 | Germany . |
| 1275173 | 5/1972 | United Kingdom . |
| 9203120 | 3/1992 | WIPO . |

*Primary Examiner*—Gary L. Geist
*Assistant Examiner*—Joseph D. Anthony
*Attorney, Agent, or Firm*—Cushman Darby & Cushman

[57] ABSTRACT

Granulated bleaching composition, which may especially be used for bleaching hair, in which the granules have been obtained by granulation of a mixture of its various pulverulent constituents by means of two binders: a first binder chosen from the group formed by polyvinyl alcohol, homo- and copolymers of vinylpyrrolidone and their mixtures and a second binder chosen from the group formed by polyalkylene glycols in which the alkylene group is $C_2$ to $C_4$ and which have a molecular weight between 200 and 30,000, and their mixtures, the granules having a particle size between 65 $\mu$m and 800 $\mu$m.

14 Claims, No Drawings

BLEACHING COMPOSITION IN GRANULATED FORM WHICH MAY BE USED FOR BLEACHING HAIR AND PROCESS FOR THE PREPARATION OF THE SAID COMPOSITION

The present invention relates to a bleaching composition in granulated form based on peroxidized derivatives, which may especially be used for bleaching hair, and a process for the preparation of the said composition.

It is known to bleach hair with the aid of a paste obtained by mixing, at the time of application to the hair, a bleaching composition based on peroxidized derivatives with water or, better still, with hydrogen peroxide. The bleaching composition consists, in a known manner, of a peroxidized derivative, generally a persulphate or a perborate of sodium, potassium or ammonium and sometimes a percarboxylic acid salt or a peroxide of, for example, barium or strontium. These compositions also contain, in a known manner, strongly alkaline agents such as alkali metal or alkaline-earth metal metasilicates, phosphates or carbonates; they may also contain other additives: agents for controlling the release of oxygen during the mixing with hydrogen peroxide, such as magnesium carbonate or magnesia; surface-active agents, such as fatty alcohol sulphates, alkyl sulphates and alkylbenzenesulphonates; thickening agents, such as cellulose derivatives, for example carboxymethyl cellulose, starch and its derivatives, guar gum, xanthan gum and alginates; blue or violet coloring agents and perfumes. Such bleaching compositions are described, for example, in "The science of hair care" by C. Zviak, Marcel Dekker Inc. 1986, pages 225 and 226.

The bleaching composition is often used in the form of a powder of small particle size, which makes possible an easy and rapid dissolution in hydrogen peroxide. However, these pulverulent compositions have several disadvantages. In the first place, the pulverulent compositions consist of powders having different apparent densities and, in the course of their handling and their storage, separation of the constituents occurs, the heavier collecting at the lower part of the packaging in which the composition is contained and the lighter in the upper part; as a consequence, during withdrawal of the composition in order to mix it with hydrogen peroxide, the volumes taken at the upper part of the packaging and those taken at the lower part have different compositions and, therefore, a different bleaching power. In the second place, the compositions in pulverulent form give off, during their handling, dusts which contain peroxidized derivatives and are, as a consequence, strongly irritating to the lungs.

In order to resolve this problem, it has already been proposed to place the bleaching composition in granulated form.

According to WO-A 92/03120, it has been proposed to granulate a persulphate and to mix it with optionally granulated particles of the various other constituents of the composition. Granulation of the persulphate may be performed either by spraying and drying an aqueous persulphate solution optionally containing surface-active agents or water-soluble thickening agents, or by spraying a solution of surface-active agent or of thickening agent onto a moving bed of solid persulphate. If this process, as presumed, makes it possible to avoid the formation of irritating persulphate dusts, it certainly does not make it possible to resolve the problem of the separation of the particles of the various constituents of the bleaching composition.

In FR-A 2,044,324, it has been proposed to granulate the constituents of the pulverulent bleaching composition collectively with the aid of a binder: polyvinylpyrrolidone or glucose dissolved in an aqueous, aqueous-alcoholic or alcoholic medium. The problem of the separation of the various constituents of the bleaching composition is thereby resolved, since the various constituents are present in the same granule. However, it has been observed that the use of polyvinylpyrrolidone alone as binder gives hard, but nevertheless crumbly, granules which, on repeated rubbing, form fine dusts which are capable of being carried into the atmosphere. Furthermore, granules of high particle size between 1 and 6 mm are obtained, which increases the dissolution time and gives, on mixing with hydrogen peroxide, a paste which remains granular for a long time and the application of which is unpleasant; furthermore, on application to hair this paste runs the risk of giving inhomogeneous and non-reproducible bleaching.

According to the present invention, it has been found that by no longer using a single binder, but two binders, the first being a homopolymer and/or a copolymer of vinylpyrrolidone or polyvinyl alcohol and the second a polyalkylene glycol, not only was the problem of separation of the various constituents avoided, but also granules were obtained which form practically no dust by rubbing and, which, when their particle size is between 65 μm and 800 μm, dissolve readily in hydrogen peroxide to give a homogeneous and creamy paste which is easy to apply to hair. In addition, it should be noted that it is possible to grind the granules having a particle size greater than 800 μm without any irritant dust being formed.

As a consequence, the subject of the present invention is a granulated bleaching composition which may be used for bleaching hair, in which the granules have been obtained by granulation of a mixture of its various pulverulent constituents by means of a granulation agent, characterized in that the said granulation agent comprises two binders: a first binder chosen from the group formed by polyvinyl alcohol, homo- and copolymers of vinylpyrrolidone and their mixtures and a second binder chosen from the group formed by polyalkylene glycols in which the alkylene group is $C_2$ to $C_4$ and which have a molecular weight between 200 and 30,000 and their mixtures, the granules having a particle size between 65 μm and 800 μm.

According to the present invention, the first binder may thus not only consist of the vinylpyrrolidone homopolymers used in FR-A 2,044,324 but also the vinylpyrrolidone copolymers and polyvinyl alcohol. The first binder is preferably polyvinyl alcohol.

The second binder may be any polyalkylene glycol (or mixture of polyalkylene glycols) in which the alkylene group is $C_2$–$C_4$, having a molecular weight between 200 and 30,000. A polypropylene glycol having a molecular weight between 2000 and 8000 or a polyethylene glycol having a molecular weight between 200 and 4000, more particularly between 200 and 600, is advantageously used.

The overall content of first and second binders preferably does not exceed 25% by weight relative to the total weight of the composition. The concentration of each of the binders is advantageously between 2 and 20% by weight relative to the total weight of the composition: this concentration is preferably from 2 to 8% by weight for the first binder, especially when the latter is a polyvinyl alcohol or a vinylpyrrolidone/vinyl acetate copolymer, and from 4 to 15% by weight for the second binder, especially when the latter is polypropylene glycol.

According to the invention, the granulated composition must have a particle size between 65 μm and 800 μm. In fact, when the particle size is greater than 800 μm the granules begin to dissolve in the hydrogen peroxide with difficulty and their dissolution cannot be made complete; the paste obtained is granular and not homogeneous. When the composition has a particle size lower than 65 μm, irritant dusts are formed during the handling of the bleaching composition in granulated form.

According to the present invention, it has also been found that easier dissolution in hydrogen peroxide is achieved for granulated bleaching compositions containing at least one lubricating agent from the family of cellulose derivatives, preferably sodium carboxymethyl cellulose or hydroxypropylmethyl cellulose and/or at least one lubricating agent from the family of alkali metal or alkaline-earth metal or polyol stearates. The polyol stearates are preferably chosen from glycol stearate and glycerol stearate. A mixture of potassium stearate and glycerol stearate is preferably used. In fact, in the presence of lubricating agent(s), the granules are less hard and less crumbly. The quantity of cellulose derivative(s) present as lubricant is advantageously between 1 and 10% by weight relative to the total weight of the composition, preferably 2 to 6%; the quantity of stearate(s) present is advantageously between 0.1 and 5% by weight relative to the total weight of the composition, preferably 0.2 and 1%; the overall quantity of lubricating agent is advantageously between 1 and 10% by weight relative to the total weight of the composition.

Granulation of the pulverulent mixture containing the various constituents of the bleaching composition may be performed by simultaneously dissolving in a solvent the first binder consisting of a vinylpyrrolidone homoor copolymer or the polyvinyl alcohol (or their mixtures) and the second binder consisting of a polyalkylene glycol (or a mixture of polyalkylene glycols) and by spraying the solution obtained onto a moving bed of the pulverulent mixture, advantageously homogenized beforehand, the solvent being subsequently removed.

Another mode of granulation is, however, preferred in which the first binder is introduced into the pulverulent mixture, the mixture is preferably homogenized, the second binder, dissolved in a solvent, is sprayed onto a moving bed of the mixture obtained and the solvent is removed. This process makes it possible to obtain granules of more homogeneous particle size and, in particular, avoids the formation of fines having a particle size lower than 65 μm. The quantity of granules having a particle size greater than 800 μm is low and they can be reground virtually without fines being produced. In order to regulate the particle size to the desired value, the granulation time may be altered.

The solvent may be any solvent which is compatible with the binder(s) which is (are) dissolved therein. Nevertheless, the use of an aqueous medium (water or an aqueous-alcoholic medium for example) is avoided because the presence of water may initiate decomposition of the peroxidized derivatives and, when the bleaching composition contains an ammonium derivative (for example ammonium persulphate), may result in release of ammonia. The solvent is preferably a $C_1$-$C_4$ alkanol or methylene or ethylene chlorides, or a mixture of these compounds.

When a lubricating agent is used, the latter is introduced into the pulverulent mixture.

The moving bed for the pulverulent mixture onto which the binder solution is sprayed may be any moving bed known for granulation: it may be a bed obtained in a tank with the aid of stirrers, especially blades or beaters, a bed obtained in a rotating drum or a bed obtained with the aid of a stream of ascending gas, such as a fluidized bed.

The pulverulent mixture is preferably homogenized before spraying of the binder solution. This homogenization may be carried out in a subsidiary mixer or in the moving bed before spraying. For example, in the case where the granulation is carried out in a tank, all the pulverulent constituents of the mixture are introduced into the tank and the mixture is homogenized by stirring in the tank before spraying the binder solution, and the stirring is continued, after having modified the conditions, where appropriate, in order to maintain the mixture to be granulated in the form of a moving bed during the spraying and granulation. When granulation is carried out on a fluidized bed, the pulverulent mixture to be granulated may be homogenized by stirring in a subsidiary tank, before introduction of the said mixture into the fluidized bed granulator.

The granulation may be carried out in discontinuous or in continuous fashion.

After granulation a separation is carried out, where appropriate, on the one hand of the fines having dimensions less than 65 μm, it being possible for these fines to be recycled, and on the other hand of the particles having dimensions greater than 800 μm, which are ground without resulting in formation of irritant dusts; the product obtained after grinding and classification is introduced, according to its particle size, either into the pulverulent mixture or into the finished product.

The examples below, given by way of illustration and without any limitation whatsoever being implied, will allow a better understanding of the invention.

I—Preparation of the granules

EXAMPLES 1 to 7

A "ROTO 50 P" granulator marketed by the Italian company "ZANCHETTA & C" is used, containing a 50-liter tank fitted with a lid equipped with rotating knives and a spraying nozzle, and fitted with a three-blade stirrer at the bottom of the tank, a jacket, a vacuum pump and a system for tipping the tank by ±90°.

15 kg of the pulverulent mixture containing the first binder (polyvinyl alcohol (PVA) sold under the name "POWAL 224" by the company "KURARAYS" or copolymer of vinylpyrrolidone and vinyl acetate (PVP/VA) sold under the name "LUVISKOL VA 64 POUDRE" by the company "BASF") and having the composition given (in % by weight) in the first thirteen lines of Table I are introduced into the tank. The mixture is homogenized for 5 minutes with the aid of a three-blade stirrer rotating at 200 revolutions/minute and knives turning at 1000 revolutions/minute. The knives are stopped and the stirring is continued with the aid of the three-blade stirrer after having brought its rotation speed to 160 revolutions/minute.

During this time, a solution of the second binder (polyethylene glycol of molecular weight 400 (PEG 400) and/or polypropylene glycol of molecular weight 2000 (PPG 2000)) in dichloromethane is prepared; this solution is obtained by mixing the second binder and dichloromethane in an amount of 1.5 kg of second binder for one liter of dichloromethane.

As soon as the knives have been stopped as indicated above the solution of the second binder is sprayed onto the pulverulent bed contained in the granulator in a sufficient quantity to introduce into the granulator the weight of second binder desired as indicated in % by weight in the fourteenth and fifteenth lines of Table I.

When the spraying is finished, the rotation speed of the blades is brought to 200 revolutions/minute and the knives are made to rotate at 1200 revolutions/minute until a power surge for the stirrer motors is obtained, which corresponds to the end of the granulation.

The vacuum pump is switched on, the granulator is tipped up by 90° (the axis of the tank is then almost horizontal) and the jacket is heated in order to obtain a temperature which does not exceed 40° C. in the granule bed in order to remove the solvent.

EXAMPLE 8

The same "ROTO 50 P" granulator is used as in Examples 1 to 7.

15 kg of the pulverulent mixture having the composition given (in % by weight) in the first thirteen lines of Table I are introduced into the tank. The mixture is homogenized for 5 minutes with the aid of a three-blade stirrer rotating at 200 revolutions/min and knives rotating at 1000 revolutions/min. The knives are stopped and the stirring is continued with the aid of the three-blade stirrer after having brought its rotation speed to 160 revolutions/min. During this time, a solution of two binders (polyethylene glycol of molecular weight 400 (PEG 400) and copolymer of vinylpyrrolidone and vinyl acetate sold under the name "LUVISKOL VA 64 POUDRE" by the company "BASF") in dichloromethane is prepared.

As soon as the knives have been stopped, the solution of the two binders is sprayed onto the pulverulent bed contained in the granulator in a sufficient quantity to introduce into the granulator the weight of binders desired as indicated in % in the fourteenth and fifteenth lines of Table I.

The procedure is finished as indicated in Examples 1 to 7.

II—Tests on the granules obtained according to Examples 1 to 8

The following tests were carried out:
a) Measurement of the particle size in the calibration apparatus marketed under the name "FC" by the Italian company "ZANCHETTA & C"
b) Test of the dissolution of the grains.

10 g of granulated bleaching powder are taken and placed into a non-metallic bowl. It is made into a paste with 10 g of 30-volume hydrogen peroxide, using a spatula. The total dissolution time is determined by observation with the naked eye of the paste obtained, the maximum time being 30 minutes.

c) Measurement of the volatility 10 g of granulated powder from the various samples of granulated powder are weighed into glass pots.

Stirring is carried out in the same manner (three complete cycles from low to high and vice versa) and the dust cloud which remains is evaluated visually by taking into account the density of the cloud, its persistence and the size of the particles in suspension. A volatility scale is defined which ranges from 0 to 5, the value 0 corresponding to a non-volatile powder and 5 to a very volatile powder.

The results for these various tests are given in the last three lines of Table I below.

TABLE I

| Starting Materials | Ex. 1 | Ex. 2 | Ex. 3 | Ex. 4 | Ex. 5 | Ex. 6 | Ex. 7 | Ex. 8 |
|---|---|---|---|---|---|---|---|---|
| Potassium persulphate | 45 | 45 | 45 | 45 | 45 | 45 | 45 | 45 |
| Sodium persulphate | 7.5 | 7.5 | 7.5 | 7.5 | 7.5 | 7.5 | 7.5 | 7.5 |
| Anhydrous sodium metasilicate | 11 | 11 | 11 | 11 | 11 | 11 | 11 | 11 |
| Ammonium chloride | 5 | 5 | 5 | 5 | 5 | 5 | 5 | 5 |
| Guar gum | 1 | 1 | 1 | 1 | 1 | 1 | 1 | 1 |
| EDTA acid | 1 | 1 | 1 | 1 | 1 | 1 | 1 | 1 |
| Hydrophilic silica | 4 | 4 | 4 | 3 | 3 | 3 | 3 | 4 |
| Titanium oxide | 1 | 1 | 1 | — | 0.5 | 0.5 | 0.5 | 1 |
| Sodium carboxymethyl cellulose | — | — | — | 5 | 1.7 | 1.7 | 1.5 | 2 |
| Mixture of glycerol stearate and potassium stearate (93/7 by weight) | — | 0.2 | 1 | — | 0.5 | 0.5 | 0.5 | 0.5 |
| Colloidal silica | 8.5 | 8.3 | 7.5 | 9.5 | 4.8 | 2.8 | — | 6 |
| PVP/VA (1st binder) | 6 | 6 | 6 | 6 | — | — | — | 6 |
| PVA (1st binder) | — | — | — | — | 4 | 6 | 4 | — |
| PEG 400 (2nd binder) | 10 | 10 | 10 | 6 | — | 5 | — | 10 |
| PPG 2000 (2nd binder) | — | — | — | — | 15 | 10 | 20 | — |
| Particle size (in μm) | 200 | 200 | 200 | 350 to 700 | 180 | 200 to 350 | 200 | 180 to 800 |
| Dissolution time (min) | 8 | 8 | 12 | 8 | 5 | 5 | 7 | 5 |
| Volatility | 1 | 1 | 0.5 | 0 | 0 | 0 | 0.5 | 0.5 |

EDTA acid: ethylenediaminetetraacetic acid (sequestering agent)

EXAMPLES 9 and 10

Comparative tests were carried out with powders granulated by the process described for Examples 1 to 7, using only a single binder: a polyvinylpyrrolidone polymer (PVP) sold under the name "LUVISKOL K 30" by the company "BASF" or a polyethylene glycol of molecular weight 400 (PEG 400). The same tests as for Examples 1 to 8 were carried out on the granules obtained. The formulation of the granulated composition (in % by weight) and the results of the tests are given in Table II below:

TABLE II

| Starting materials | Example 9 | Example 10 |
| --- | --- | --- |
| Potassium persulphate | 40 | 50 |
| Sodium persulphate | 9 | 7.5 |
| Anhydrous sodium metasilicate | 10 | 10.8 |
| Ammonium chloride | 5 | 4 |
| Guar gum | — | 1 |
| Ethylenediaminetetraacetic acid | 2 | 1 |
| Hydrophilic silica | — | 3 |
| Titanium oxide | — | — |
| Sodium carboxymethyl cellulose | 5 | — |
| Mixture of glycerol stearate and potassium stearate (93/7 by weight) | — | 0.5 |
| Colloidal silica | 17 | 10.2 |
| PVP | 12 | — |
| PEG 400 | — | 12 |
| Particle size (in pm) | >1000 | 65 to 1000 |
| Dissolution time (min) | >60 | 30 |
| Volatility | 1 | 1.5 |

These tests show that when a single binder is used the dissolution time of the granules is higher, the particle size of the granules is too high or too dispersed and the formation of dust is relatively high.

We claim:

1. A granulated hair bleaching composition constituted by granules, each of said granules containing said hair bleaching composition comprising:
   (a) an effective amount of a peroxidized derivative to effect bleaching of hair,
   (b) an amount of an alkaline agent, and
   (c) a granulation agent comprising first and second binders,
   said first binder being selected from the group consisting of polyvinyl alcohol, a homopolymer of vinylpyrrolidone, a copolymer of vinylpyrrolidone and a mixture thereof, and
   said second binder selected from the group consisting of a polyalkylene glycol wherein the alkylene group is a $C_2$ to $C_4$ group, having a molecular weight ranging from 200 to 30,000, said granules having a particle size between 65 and 800 μm and said granulation agent being present in an amount not exceeding 25 weight percent of the total weight of said composition.

2. The hair bleaching composition of claim 1 wherein said peroxidized derivative is a persulphate or perborate of sodium, potassium, or ammonium, a percarboxylic acid salt of barium or strontium, or a peroxide of barium or strontium.

3. The bleaching composition of claim 1 wherein said alkaline agent is an alkali metal or alkaline earth metal metasilicate, phosphate or carbonate.

4. The hair bleaching composition of claim 1 wherein said first binder is a polyvinyl alcohol.

5. The hair bleaching composition of claim 1 wherein said second binder is a polypropylene glycol having a molecular weight between 200 and 8,000.

6. The hair bleaching composition of claim 1 wherein said second binder is a polyethylene glycol having a molecular weight between 200 and 4,000.

7. The hair bleaching composition of claim 1 wherein said second binder is a polyethylene glycol having a molecular weight between 200 and 600.

8. The hair bleaching composition of claim 1 wherein each of said first and second binders is present in an amount ranging from 2 to 20 weight percent based on the total weight of said composition.

9. The hair bleaching composition of claim 8 wherein said first binder is present in an amount ranging from 2 to 8 weight percent based on the total weight of said composition.

10. The hair bleaching composition of claim 1 which contains at least one lubricating agent selected from the group consisting of a cellulose derivative and a stearate.

11. The hair bleaching composition of claim 10 wherein said lubricating agent is a cellulose derivative selected from the group consisting of sodium carboxymethyl cellulose and hydroxypropylmethyl cellulose.

12. The hair bleaching composition of claim 11 wherein said cellulose derivative lubricating agent is present in an amount ranging from 1 to 10 percent by weight based on the total weight of said composition.

13. The hair bleaching composition of claim 10 wherein said lubricating agent is selected from the group consisting of an alkali metal stearate, an alkaline earth metal stearate and a polyol stearate.

14. The hair bleaching composition of claim 13 wherein said stearate is present as a lubricating agent in an amount ranging from 0.1 to 5 percent by weight relative to the total weight of said composition.

* * * * *